United States Patent [19]

Quinlan

[11] 4,153,678

[45] May 8, 1979

[54] LEVAMISOLE EFFERVESCENT TABLETS

[75] Inventor: James M. Quinlan, Trenton, N.J.

[73] Assignee: American Cyanamid Company, Stamford, Conn.

[21] Appl. No.: 925,658

[22] Filed: Jul. 17, 1978

[51] Int. Cl.² .................... A61K 31/425; A61K 47/00
[52] U.S. Cl. ........................................ 424/44; 424/270
[58] Field of Search .................................. 424/44, 270

[56] References Cited

U.S. PATENT DOCUMENTS 3,577,491   5/1971   Cox ........................................ 424/44
3,584,099   6/1971   Hoss ....................................... 424/44

Primary Examiner—Sam Rosen
Attorney, Agent, or Firm—Harry H. Kline

[57] ABSTRACT

There are provided levamisole effervescent tablets which comprise a composition characterized by excellent solubility yielding crystal clear solutions in water, good storage stablity, and ease of use. There are also provided methods for the oral administration of levamisole to swine in predetermined dosages via the drinking water offered to said animals utilizing the aforesaid levamisole effervescent tablets.

5 Claims, No Drawings

LEVAMISOLE EFFERVESCENT TABLETS

The present invention relates to levamisole effervescent tablets or compositions characterized by excellent solubility yielding crystal clear solutions in water, good storage stability, and ease of use. Further, the present invention relates to methods for the oral administration of levamisole to swine in predetermined dosages via the drinking water given to said animals utilizing levamisole effervescent tablets hereinafter defined with particularity.

Effervescent tablets, granules and powders have been in use for sometime for the administration of medication to humans and/or for the preparation of antacid solutions and mildly carbonated beverages.

The use of effervescent tablets and the like in veterinary medicine for treating swine, however, has not been contemplated or disclosed in the prior art as far as it can be determined.

Thus the levamisole effervescent tablets of the present invention are novel and hitherto undisclosed.

Levamisole, 1-6-phenyl-2,3,5,6-tetrahydroimidazo-[2,1-b]thiazole, and its pharmaceutically acceptable salts, such as the hydrochloride, are much sought after for the control of helminths infesting swine.

Levamisole may be formulated for oral administration as feed concentrates, feed additives, tablets, boluses, oral drenches and the like, or it may be administered in the form of injectables.

Although these formulations usually perform satisfactorily, some of them such as the feed concentrates and feed additives are more suitable for large scale use and would be too expensive and/or impractical for use by the small operator. Other formulations, such as tablets, boluses, oral drenches, injectables and the like, though suitable for use on a small scale, are cumbersome and tedious to administer.

Thus there is a need for an accurately premeasured dosage form which dissolves rapidly to give a homogeneous solution without mechanical agitation and would allow the oral administration of the above anthelmintic with ease.

Surprisingly, it has been found that the novel levamisole effervescent tablets of the present invention are eminently suitable for oral administration of said anthelmintic in premeasured dosages to swine via said animals' drinking water.

Attempts to incorporate levamisole in conventional effervescent tablettable formulations comprising citric acid, sodium bicarbonate and a water insoluble tabletting lubricant, such as magnesium stearate, have not been completely successful. The tablets obtained lack storage stability and decompose rapidly even in the absence of moisture when stored both at 37° C. and at 45° C. as evidenced by marked discoloration and stickiness of the tblets after only about two weeks of storage at the above temperatures. Thus, such formulations are clearly not satisfactory.

It is found that levamisole hydrochloride in the solid state is not compatible with many of the pharmaceutically acceptable acids. Thus, blends of levamisole hydrochloride with acids such as citric, maleic, malic, succinic and tartaric acids, stored in air-tight containers at both 37° C. and at 45° C. for a period of 1 to 4 weeks exhibit caking, lumping, and discoloration. On the other hand, blends of levamisole hydrochloride with adipic and fumaric acids exhibit little or no caking and no discoloration when stored at the above temperatures for a period of four weeks. Though both of the latter acids are compatible with levamisole hydrochloride, the use of adipic acid is preferred in the effervescent tablets of the present invention due to its greater inherent solubility in water and very low hygroscopicity.

Surprisingly, adipic acid is found to be a suitable replacement for water insoluble solid lubricants, such as magnesium stearate which, although being the most efficient of tablet lubricants, are not suitable for incorporation in the effervescent tablets of the present invention, since such lubricants are not soluble in water. Thus, when said tablets are dissolved in water, the presence of a water insoluble lubricant will produce a highly unsightly surface film.

In practice, it is preferred that the novel effervescent compositions hereinabove-defined be granulated prior to being compressed into tablets, since granular formulations are more suitable for loading the tablet presses and also offer good compressability. Moreover, polyvinylpyrrolidone (PVP), usually from 1% to 10% by weight and, preferably, from 3% to 7% by weight is satisfactory for use as a binder and granulating agent. Since PVP is soluble in non-aqueous solvents, such as methylene chloride or 2-propanol, an otherwise two step granulation process wherein levamisole hydrochloride, adipic acid and sodium bicarbonate are separately granulated with an aqueous solution of PVP, followed by drying and blending, can be combined into a single granulation step. Considering that the presence of even small amounts of moisture in the finished granulation and the tablets obtained therefrom is detrimental to the storage stability of said effervescent tablets, it is of marked importance to utilize a binder-granulating agent that is soluble in non aqueous solvents.

Advantageously, the effervescent tablets of the present invention can be prepared by admixing from about 10% to about 50%, by weight, and, preferably, from 20% to 30% by weight of a pharmaceutically acceptable water soluble salt of levamisole, such as the hydrochloride, sodium bicarbonate and adipic acid in approximately 1:1 weight ratio making up the balance of the formulation. To the resultant mixture is added a solution of from 1% to 10% by weight and, preferably, from 3% to 7% by weight of polyvinylpyrrolidone (wherein the amount of sodium bicarbonate-adipic acid is reduced by a corresponding weight percent) in methylene chloride and the mix is granulated to 8 to 12 mesh size on an oscillating granulator. The wet granulation is then dried in vacuo at 30° C. to 40° C. for a period of 10 to 20 hours. Next, from 3% to 10% by weight and, preferably, from 5% by weight of adipic acid is added (compensated for by a corresponding weight percent reduction of the total amount of sodium bicarbonate-adipic acid present in the blend) to the dry granulation as a solid tabletting lubricant, the mixture is thoroughly blended, and regranulated, if so desired. The so-prepared granulation is compressed on a tabletting machine to obtain tablets having a diameter ranging from 2.5 cm to 5.0 cm and weighing from 3 to 15 g each and containing levamisole sufficient to medicate from 7.0 liters to 20.0 liters of water so as to treat from about 113.00 kg to about 230 kg of pig.

It is found that a preferred effervescent tablet can be prepared in a straightforward manner by blending, for instance, 26% by weight of dry levamisole hydrochloride, 34% by weight of dry sodium bicarbonate and 30%, by weight, of dry adipic acid in a suitable blender, such as a twin shell blender. Next, a solution of 5% by weight of polyvinylpyrrolidone in methylene chloride is added and the mixture agitated to form granules, and is then further granulated on an oscillating granulator, to obtain a granulation of 8 to 12 mesh size. The so-obtained wet granulation is air dried to remove the bulk of methylene chloride, and is then dried in vacuo at 34° C. to 45° C. for a period of 10 to 20 hours to remove residual solvent and any moisture present in the granulation.

To minimize detrimental moisture pick-up during the granulation and the subsequent tabletting step, the process is preferably carried out under controlled atmospheric conditions where the relative humidity does not exceed 20%. The so-obtained granulation is compressed into tablets of desired size and weight. The tablets are packaged without delay in aluminum foil pouches laminated both in and outside with inert polymeric materials such as polyethylene, polyester and the like for optimum stability. Other containers with good water vapor barrier properties, e.g. glass bottles and vapor proof closures are acceptable. Under these conditions the residual moisture in the tablets is 0.1% or less, and the tablets may be stored in a cool place for a period of up to two years without significant loss of potency and/or decomposition. Resultant tablets possess sufficient hardness and will disintegrate in water at 24° C. in about 3.5 to 4.5 minutes to give crystal clear sparkling solutions.

Advantageously, the levamisole effervescent tablets prepared by any of the hereinabove described processes dissolve rapidly in water, the tablets being heavier than water and will sink to the bottom of the watering trough used to offer drinking water to swine and the carbon dioxide gas evolving vigorously during the dissolution of the tablets will sufficiently agitate the water so that a uniform solution of levamisole hydrochloride in water is obtained without the need to mechanically stir said solution.

In general, the novel levamisole effervescent tablets of the invention are well suited for use by the small operator for the control of helminths in swine. According to his needs and as the circumstances dictate, he can dissolve one or more tablets in the drinking water and offer the thus-medicated water to said animals to be treated. The animals need not be handled or restrained in any way as would be the case with orally administered tablets, boluses or drenches, or with injectables. Consumption of the drug by the animals is easily supervised and the animal can be compelled to consume the full dosage since additional drinking water may be withheld until the medicated drinking water is consumed in its entirety.

The following non-limiting examples serve to further illustrate the invention.

EXAMPLE 1

Preparation of Dry Lubricant Blend

Polyvinylpyrrolidone (PVP; 150.0 g) and polyethylene glycol (PEG-6000; 100.0 g) are mixed, blended and put through a #100 mesh screen. The screened material is reblended to yield 250.0 g of 60:40% w/w PVP:PEG 6000 dry lubricant blend.

EXAMPLE 2

Preparation of a Levamisole-adipic Acid Blend

Levamisole hydrochloride (1235 g) and food grade adipic acid (micromilled; 1362 g) are mixed, and passed through a mill to yield 2597.0 g of a blend, containing 47.55% w/w levamisole hydrochloride.

EXAMPLE 3

Preparation of Granulated Sodium Bicarbonate

Polyvinylpyrrolidone (100.0 g) is dissolved in methylene chloride (1425 ml), the solution is added to sodium bicarbonate (Church & Dwight, gran #5; 2850.0 g) and the mixture agitated to form granules. The wet granulation is passed through an 8 mesh screen using an oscillating granulator, and dried at 40° C. for 48 hours.

EXAMPLE 4

Preparation of a Levamisole-adipic Acid Granulation

Adipic acid (micromilled; 1036.0 g), and levamisole hydrochloride (863.5 g) are placed in a suitable mixer bowl, and mixed for ten minutes. Next, a solution of polyvinyl-pyrrolidone (100.0 g) in methylene chloride (950 ml) is added to the blended powders and the mixture agitated to form granules. The wet granulation is passed through an 8 mesh screen using an oscillating granulator. The wet granules are dried overnight and at 60° C. for 48 hours. There are obtained 2000 g of granulation containing 43.18% levamisole hydrochloride by weight.

EXAMPLE 5

Preparation of a Levamisole-adipic Acid Granulation

To a blend of levamisole hydrochloride-adipic acid (1900.0 g) obtained by the process of Example 2, a solution of polyvinylpyrrolidone (100.0 g) in methylene chloride (950 ml) is added and the mixture agitated to form granules. The wet granulation is passed through an 8 mesh screen. The wet granules are air-dried overnight and then at 60° C. for 48 hours. There are obtained 2000 g of granulation containing 45.17% levamisole hydrochloride by weight.

EXAMPLE 6

Preparation of Levamisole HCl Effervescent Tablets

Levamisole HCl-adipic acid granulation (1465.0 g) obtained by the process of Example 4 above, sodium bicarbonate granulation (952.0 g) of Example 3 above, and the solid lubricant (24.0 g) of Example are mixed, passed through an oscillating granulator and pressed into oblong (2"×13/16") tablets weighing approximately 15.0 g each. Randomly selected tablets are stored in well-capped clear glass bottles at room temperature and at 37° C. Samples are assayed initially and 3 months later. The data obtained are summarized in Table I below.

Table I

Determination of the Chemical Stability of Levamisole HCl Effervescent Tablets

| Assay | Storage at | | | |
|---|---|---|---|---|
| | Room Temperature | | 37° C. | |
| | Initial | 3 Months | Initial | 3 Months |
| Percent w/w | 24.5 | 22.7 | 24.5 | 22.5 |
| levamisole HCl | 22.8 | 23.2 | 22.8 | 23.1 |
| Hardness in kg | 37.3 | 34.5 | 37.3 | <43.5 |
| | | 25.5 | | <43.5 |
| Disintegration in | 5.5 | 3.5 | 5.5 | 4.5 |
| Water at 22° C./min. | | 3.5 | | 4.5 |

EXAMPLE 7

Preparation of Levamisole HCl Effervescent Tablets

Sodium bicarbonate (1050.0 g), levamisole hydrochloride (98% real; 780.0 g) and food grade adipic acid (milled; 1020.0 g) are charged to a suitable mixer bowl and are thoroughly mixed. Next, a solution of polyvinylpyrrolidone (150.0 g) in methylene chloride (1425 ml) is added and the mixture agitated to form granules. The wet granulation is passed through a 10 mesh screen using an oscillating granulator. The wet granules are dried at 37° C. to 43° C. for 16 hours in vacuo, and are then pressed into oblong tablets, weighing approximately 15 g each. Initial mean hardness of the tablets is 35.5 kg, and the disintegration time in water at 22° C. is 5 minutes.

Samples stored for two years at room temperature retain 97.5% of initial potency.

EXAMPLE 8

Preparation of Levamisole HCl Effervescent Tablets

Levamisole HCl-adipic acid granulation (2980.0 g) obtained by the process of Example 4, sodium bicarbonate granulation (1937.0 g) of Example 3, and the solid lubricant (50.0 g) of Example 1 are mixed, passed through an oscillating granulator and formed on a press into oblong (2"×13/16") tablets, weighing approximately 15.0 g each. Randomly selected tablets are stored in well-capped clear glass bottles at room temperature and at 37° C. Samples are assayed initially and 3 months later. The data obtained are summarized in Table II below.

TABLE II

Determination of the Chemical Stability of Levamisole Effervescent Tablets

| | Storage at | | | |
|---|---|---|---|---|
| | Room Temperature | | 37° C. | |
| Assay | Initial | 3 Months | Initial | 3 Months |
| Percent w/w levamisole HCl | 21.9 | 19.6 | 21.9 | 20.0 |
| | 20.5 | 19.4 | 20.5 | 20.0 |
| Hardness in kg | 33.5 | 34.5 | 33.5 | 43.5 |
| | | 34.5 | | 43.5 |
| Disintegration in Water at 22° C., in a minute | 4.5 | 2.5 | 4.5 | 3.75 |
| | | 3.0 | | 4.0 |

EXAMPLE 9

Evaluation of the Thermal Stability of an Effervescent Composition Containing Levamisole Hydrochloride.

Levamisole hydrochloride (250.0 g), anhydrous citric acid (granular; 500.0 g), sodium bicarbonate (Church and Dwight gran. #5; 245.0 g) and magnesium stearate (5.0 g) are blended, put through a #4 mesh screen, reblended and pressed into oblong (2"×13/16") tablets, weighing approximately 15 g each, for thermal stability tests. Randomly selected tablets are stored in well-capped clear glass bottles at room temperature, at 37 and at 45° C. The samples are examined once weekly for signs of decomposition, surface changes and/or gas evaluation. The data obtained are summarized in Table III below.

Table III

Thermal Stability of an Effervescent Composition Containing 25% by Weight of Levamisole HCl

| Week | Room Temperature | 37° C. | 45° C. |
|---|---|---|---|
| Initial | Smooth, white tablets | Smooth, white tablets | Smooth, white tablets |
| 1 | No change | No change | Darker color, tablets stuck together; Wet, sticky |
| 2 | No change | Surface trace sticky; No gas pressure | Darker color, tablets stuck together; wet, sticky & shiny no gas pressure |
| 3 | No change | Surface trace sticky; No gas pressure | Darker color, tablets stuck together; Wet sticky & shiny no gas pressure |
| 4 | No change | Surface rough, beaded, sides beginning to cap; No gas pressure | Very rough beaded surface tablets stuck firmly together; dark |

EXAMPLE 10

Preparation of Effervescent Tablets Containing 26% by Weight of Levamisole HCl I. Preparation of the effervescent granulations Levamisole hydrochloride (1) sodium bicarbonate (2) and food grade adipic acid (3) are placed in a suitable mixer bowl and blended for ten minutes. Next, a solution of polyvinylpyrrolidone (4) in methylene chloride (6) is added to the blend and the mixture agitated to form granules. The wet granulation is passed through an 8 mesh screen using a Stokes oscillating granulator. The wet granules are dried (see below), and then passed through a 10 mesh screen using a Stokes oscillating granulator. Food grade adipic acid (5) is added, the mixture is blended for 10 minutes and is then ready for compression (tabletting).

Three batches (A, B, and C) are prepared by the above procedure, the composition of the batches is given in Table IV below.

Table IV

Composition of Three Effervescent Granulations Prepared by the Above Procedure

| No. | Component | % (by weight) | Weight of Component (in kg.) | | |
|---|---|---|---|---|---|
| | | | A | B | C |
| 1 | Levamisole hydrochloride 98% real | 26.00 | 1.56 | 1.56 | 2.60 |
| 2 | Sodium bicarbonate | 34.00 | 2.04 | 2.04 | 3.40 |
| 3 | Adipic acid | 30.00 | 1.80 | 1.80 | 3.00 |
| 4 | Polyvinylpyrrolidone | 5.00 | 0.30 | 0.30 | 0.50 |
| 5 | Adipic acid | 5.00 | 0.30 | 0.30 | 0.50 |
| Total | | 100.00 | 6.00 | 6.00 | 10.00 |
| 6 | Methylene chloride, (in liters) | | 1.62 | 1.62 | 2.70 |

Ia. Drying of the above effervescent granulations

A. The total granulation is dried for 90 minutes at room temperature in an air current. Then one half of the total granulation is dried in vacuo for 90 minutes at 37° C. to 43° C. with a weight loss of 1.0% the remaining granulation is dried first in a convection oven for two hours (weight loss; 0.54%) followed by drying in vacuo at 37° C. to 43° C. overnight (weight loss; 0.82%) giving a total weight loss of 1.36%.

B. The granulation is dried in three stages with weight losses as cited below:

| | |
|---|---|
| (a) Two hours at 45° C. in a convection oven, | wt. loss: 0.21% |
| (b) Two hours at 37° C. to 43° C. in vacuo; | wt. loss: 0.38% |
| (c) 15 Hours at 37° C. to 43° C. in vacuo; | wt. loss: 0.85% |
| | Total wt. loss: 1.44% |

C. The granulation is dried at room temperature, no weight loss noted.

II. Preparation of the effervescent tablets

The above granulations are pressed on a Stokes Model R single punch press, fitted with 1.75" round, flat faced, leveled edge punches and die.

The finished tablets are packaged in aluminum foil pouches, constructed (from outside to inside) from 1 mil cellophane, 0.5 mil polyethylene, 0.35 ml aluminum foil and 1 mil polyethylene.

The physical properties of the finished tablets are summarized in Table V below.

Table V

Physical Properties of Tablets Prepared from the Above Granulations

| Tablet Property | A | B | C |
|---|---|---|---|
| Theoretical weight/g | 15.0 | 15.0 | 15.0 |
| Mean wt. actual/g | 15.75 | 14.72 | 15.48 |
| Hardness (Dillon) in kg | 63.6 | 63.6 | 63.6 |
| | No break | No break | No break |
| Diameter in cm | 4.48 | 4.48 | 4.48 |
| Thickness in cm | 0.74 | 0.73 | 0.73 |
| Disintegration time in water at 24° C./in minutes | 5.5 | 5.5 | 5.75 |
| Relative humidity of environment when compressed; in % | 49.00 | 28.00 | 35.00 |

The tablets prepared from batch C are dried in vacuo overnight with a mean weight loss of 0.4%.

The tablets prepared from batches A to C are both physically and chemically stable at room temperature and little or no loss of potency is noted after two years at room temperature as shown below:

TABLE VI

| | percent by weight of Assay:levamisole HCl Content | | |
|---|---|---|---|
| Time | A | B | C |
| Initial | 25.5 | 25.6 | 25.2 |
| 2 Years | 25.2 | 24.93 | 24.32 |

At 37° C., carbon dioxide gas produced puffing of the pouches within four weeks, even in the freshly vacuum dried and packaged sample.

EXAMPLE 11

Preparation of Effervescent Tablets Containing 26% by Weight of Levamisole HCl

I. Preparation of the effervescent granulation

Food grade adipic acid (2) and FD & C yellow dye #5 (1) are mixed and milled for 16 hours in a ball mill.

The above blend, levamisole hydrochloride (3), food grade adipic acid (4) and sodium bicarbonate (5) are charged to a mixer and blended for ten minutes. Next, a solution of polyvinylpyrrolidone (6) in methylene chloride (8) is added to the blend and the mixture agitated for 5 minutes to form granules. The wet granulation is passed through an 8 mesh screen using a Colton oscillating granulator. The wet granules are dried 8 hours at 37° C. to 43° C. in vacuo, and then passed through a 12 mesh screen using a Colton oscillating granulator. Food grade adipic acid (7) is added, the mixture is blended for ten minutes and is then ready for tabletting.

The relative humidity of the environment is maintained at or below 20% in the course of these preparations both during the granulating phase and during tabletting.

The batches are prepared by the above procedure. The composition of the batches is given in the table below.

Table VII

Composition of Three Effervescent Granulations Prepared By the Above Procedure

| No. | Component | % by Weight | Weight of Component in kg | | |
|---|---|---|---|---|---|
| | | | A | B | C |
| 1 | FD & C yellow dye #5 | 0.1 | 0.0150 | 0.030 | 0.0150 |
| 2 | Adipic acid | 0.4 | 0.060 | 0.120 | 0.060 |
| 3 | Levamisole hydrochloride 98% real | 26.0 | 3.900 | 7.800 | 3.900 |
| 4 | Adipic acid | 29.5 | 4.425 | 8.850 | 4.425 |
| 5 | Sodium bicarbonate | 34.0 | 5.100 | 10.200 | 5.100 |
| 6 | Polyvinylpyrrolidone | 5.0 | 0.750 | 1.500 | 0.750 |
| 7 | Adipic acid | 5.0 | 0.750 | 1.500 | 0.750 |
| Total | | 100.0 | 15.00 | 30.00 | 15.00 |
| 8 | Methylene chloride, in liters | | 3.875 | 7.75 | 3.875 |

II. Preparation of the effervescent tablets

The above granulations are pressed on a Colton Model 250, 12 station rotary press, fitted with 1" round, flat face leveled punches and dye - standard feed shoe and hopper.

The finished tablets are packaged in aluminum foil pouches constructed (from the outside to inside) from 0.5 ml PVDC coated polyester, 0.35 mil aluminum foil and 1.5 mil polyethylene.

The physical properties of the finished tablets are summarized in the table below.

Table VIII

Physical Properties of Tablets Prepared From the Above Granulation

| Tablet Property | A | B | C |
|---|---|---|---|
| Theoretical weight/g | 3.74 | 3.74 | 3.74 |
| Mean weight actual/g | 3.79 | 3.76 | 3.77 |
| Hardness (Stokes) in kg | 34.0 | 32.4 | 29.6 |
| Disintegration time in water at 15° C.; in minutes | — | 4.3 | — |
| Weight loss in % after 8 hours in vacuo at 37° C. to 43° C. | 0.23 | 0.13 | 0.17 |

The physical and chemical stability of the above-prepared tablets is analogous to the tablets obtained by the process of Example 10.

EXAMPLE 12

Evaluation of the Thermal Stability of Various Levamisole Hydrochloride - Organic Acid Blends Levamisole hydrochloride is blended thoroughly in a 1:1 weight ratio with tartaric acid, succinic acid, malic acid, maleic acid, fumaric acid, citric acid and adipic acid. Each blend is divided into three equal parts and the samples are stored in clear well-capped glass bottles at room temperature, 37° C. and 45° C. The samples are examined once weekly for discoloration, caking, lumping and evolution of gas. The data obtained are summarized in Tble IX below.

Table IX

Evaluation of Levamisole Hydrochloride Blends With Organic Acids

| Acid | Week | Room Temperature | 37° C. | 45° C. |
|---|---|---|---|---|
| Tartaric | 0 | Free-flowing, white powder | Free-flowing, white powder | Free-flowing white powder |
| | 1 | No change | No change | No change |
| | 2 | No change | No change | No change |
| | 4 | Trace lumpy; no gas pressure | Trace lumpy; no gas pressure | Trace lumpy; no gas pressure |
| Succinic | 0 | Free-flowing, white powder | Free-flowing, white powder | Free-flowing, white powder |
| | 1 | No change | No change | No change |
| | 2 | No change | No change | No change |
| | 4 | Trace lumpy; no gas pressure | Trace lumpy; no gas pressure | Trace lumpy; no gas pressure |
| Malic | 0 | Free-flowing, white powder | Free-flowing, white powder | Free-flowing, white powder |
| | 1 | No change | No change | No color change; trace caked; no gas pressure |
| | 2 | No change | No color change; sightly caked; no gas pressure | No color change; caked; no gas pressure |
| | 4 | Trace lumpy; no gas pressure | Trace lumpy; no gas pressure | Caked; no gas pressure |
| Maleic | 0 | Free-flowing, off white-yellowish-powder | Free-flowing, off white yellowish-powder | Free-flowing, off white-yellowish-powder |
| | 1 | Somewhat darker color, no other change | Trace caked, deeper color; no gas pressure | Deeper color; badly caked; no gas pressure |
| | 2 | Trace caked; no gas pressure | Caked, deeper color; no gas pressure | Deeper color; badly caked; no gas pressure |
| | 4 | lumpy, partially caked; no gas pressure | Caked, lumpy; increased yellowing; no gas pressure | Partially melted, lumpy solid; yellow; no gas pressure |
| Fumaric | 0 | Free-flowing, white powder | Free-flowing, white powder | Free-flowing, white powder |
| | 1 | No change | No change | No change |
| | 2 | No change | No change | No change |
| | 4 | Trace caked; no gas pressure | Trace lumpy; no gas pressure | Trace lumpy; trace gas pressure |
| Citric | 0 | Free-flowing white powder | Free-flowing, white powder | Free-flowing, white powder |
| | 1 | No change | No change | Trace caked, no gas pressure |
| | 2 | No change | No change | Trace caked, no gas pressure |
| | 4 | Sligthly lumpy; no gas pressure | Trace lumpy; no gas pressure | Trace lumpy; no gas pressure |
| Adipic | 0 | Free-flowing, white powder | Free-flowing, white powder | Free-flowing, white powder |
| | 1 | No change | No change | No change |
| | 2 | No change | No change | No change |
| | 4 | Slightly caked, no gas pressure | Slightly caked, no gas pressure | Trace lumpy; no gas pressure |

EXAMPLE 13

Evaluation of the Stability of Aqueous Levamisole Solutions Prepared From Levamisole Effervescent Tablets One levamisole HCl effervescent tablet each is added at ambient temperature to 9.46 liter well water having a pH of from 6.7 and to 9.46 liters well water, the pH of which is adjusted to 8.5. The solutions are thoroughly mixed and two 400 ml samples of each solution are taken for initial analyses. The remainder of each batch of medicated water is placed in a rusty cast iron hog water trough about 5 feet long and is contaminated with 50 g of fresh hog feces to simulate conditions that might occur in actual use. The troughs are covered with aluminum foil the prevent evaporation and are left in a barn for 24 hours at ambient temperature. After 24 hours two additional samples of each batch of medicated water are obtained for analyses. The data obtained are summarized in Table X below.

Table X

Levamisole Stability in Swine Drinking Water Under Conditons of Use

| Type of Water | Levamisole Hydrochloride mg/3.78 l | | % Recovery after 25 hrs. |
|---|---|---|---|
| | Initial | 24 Hrs. | |
| Well water, pH 6.7 | | | |
| A | 389 | 373 | |
| | 389 | 373 | 95.9 |
| B | 389 | 373 | 95.9 |
| | 389 | 373 | |
| Well water, pH 8.5 | | | |
| A | 390 | 375 | |
| | 391 | 376 | 96.2 |
| B | 392 | 375 | |
| | 391 | 373 | 95.5 |

It can be seen from the above table that the loss of potency of medicated water is less than 5% in both types of drinking water. Since medicated water is consumed within 24 hours or less, there appears to be no problem with loss of potency under conditions of use.

EXAMPLE 14

Evaluation of the Safety and Acceptability of Levamisole Effervescent Tablets for Swine When Administered in Drinking Water The effervescent tablets used in this test have the following composition (by weight):

| | |
|---|---|
| Levamisole hydrochloride | 25.74% |
| Sodium bicarbonate | 34.65% |
| Adipic acid | 33.66% |
| Polyvinylpyrrolidone | 4.95% |
| PVP: PEG 6000 (60:40) lubricant | 1.00% |

Each tablet, when added to 37.85 liters of drinking water, supplies 363 mg levamisole hydrochloride per 3.78 liters with an additional excess of 5% ($\cong$ 381 mg per 3.78 liters).

Animals

Thirty-six Yorkshire-Hampshire pigs (16 barrows and 20 gilts) are allotted to three groups with three replicates per treatment. Each pen contains 4 barrows or 4 gilts. Group I receives unmedicated drinking water (control), Group II receives drinking water medicated with levamisole soluble hog wormer at 363 mg levamisole hydrochloride per 3.78 liters of drinking water and Group III receives drinking water medicated with levamisole effervescent tablets.

The hogs are fed PC-2* swine ration containing AUREO SP-250® ad libitum and are also offered water ad libitum. One day before medication individual pig weights are recorded, and drinking water removed from the pens at 4 pm. On the following day, non-medicated control and levamisole medicated water are given in the morning. Medicated water, 3.78 liters per 45.3 kg of body weight sufficient to furnish 8 mg per kg of body weight is placed in calibrated containers. The amount of water consumed by each pen of pigs in 6 hours is recorded. The time required for complete disintegration of levamisole effervescent tablets is also recorded.

Average water consumption after 6 hours is 14.21 liters for the non-medicated controls, 18.71 liters for Group II and 17.35 liters for Group III.

No adverse reactions are noted in control or medicated pigs during or following treatment. The acceptability of the two formulations administered in drinking water is comparable to non-medicated water.

The effervescent tablets completely disintegrate in 37.85 liter of water within 5 minutes at 32° C.

| Composition of PC-2 Ration* | |
|---|---|
| Ingredients | Percent |
| Ground Yellow Corn | 76.90 |
| Soybean Oil Meal, 44% Protein | 16.25 |
| Meat and Bone Scraps, 50% Protein | 2.50 |
| Dried Whey | 2.50 |
| Dicalcium Phosphate | 1.00 |
| Iodized Salt | 0.50 |
| Ground limestone | 0.20 |
| Vitamin-trace Mineral Mix[1] | 0.15 |
| | 100.00 |

[1]Furnished the following ingredients per ton of diet:
| | | |
|---|---|---|
| Vitamin A | 3,000,000 | IU |
| Vitamin D$_2$ | 600,000 | IU |
| Riboflavin | 6 | g |
| Pantothenic acid | 15 | g |
| Niacin | 30 | g |
| Vitamin B$_{12}$ | 15 | mg |
| Menadione (Source of Vitamin K) | 3 | g |
| Iron | 75 | ppm |
| Copper | 7.5 | ppm |
| Manganese | 45 | ppm |
| Zinc | 75 | ppm |

*Contains Aureo SP-250® which supplies 100 g chlorotetracycline, 100 g sulfamethazine and 50 g penicillin per ton of finished feed.

We claim:

1. An anthelmintically effective, compressed and shaped unit dosage of a solid effervescent composition comprising a pharmaceutically acceptable water soluble salt of levamisole, an alkali metal bicarbonate, a pharmaceutically acceptable adipic or fumaric acid, a non-toxic binder and a non-toxic solid tabletting lubricant, and said composition may, additionally, also contain a pharmaceutically acceptable dye; and said unit dosage form characterized by rapidly releasing all of the above-said drug on dissolution in water with the simultaneous evolution of carbon dioxide and the formation of a clear solution of said drug.

2. The effervescent composition according to claim 1, wherein the levamisole salt is the hydrochloride, the alkali metal bicarbonate is sodium bicarbonate, the alkylene dicarboxylic acid is adipic acid, the non-toxic binder is polyvinylpyrrolidone and the solid tabletting lubricant is adipic acid.

3. The effervescent composition according to claim 1, comprising 10 to 50% by weight of levamisole hydrochloride, 1 to 10% by weight of polyvinylpyrrolidone, 0.1% by weight of a pharmaceutically acceptable, water soluble dye, 3 to 10% by weight of adipic acid tablet lubricant, and the composition is totaled to 100% by sodium bicarbonate and adipic acid in a 1 to 1 weight ratio.

4. The effervescent composition according to claim 1, comprising 26% by weight of levamisole hydrochloride, 34% by weight of sodium bicarbonate, 30% by weight of adipic acid, 5% by weight of polyvinylpyrrolidone binder and 5% by weight of adipic acid lubricant.

5. The effervescent composition according to claim 1, comprising 26% by weight of levamisole hydrochloride 34% by weight of sodium bicarbonate, 30.0% by weight of adipic acid, 0.1% by weight of water soluble yellow dye, 5% by weight of polyvinylpyrrolidone binder and 5% by weight of adipic acid lubricant.

* * * * *